U S009052260B2

(12) United States Patent
Powell

(10) Patent No.: US 9,052,260 B2
(45) Date of Patent: *Jun. 9, 2015

(54) SYSTEM, COMPONENTS, AND METHODS FOR DETECTING MOISTURE

(71) Applicant: Alan B. Powell, Lindstrom, MN (US)

(72) Inventor: Alan B. Powell, Lindstrom, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/921,203

(22) Filed: Jun. 18, 2013

(65) Prior Publication Data

US 2014/0007662 A1 Jan. 9, 2014

Related U.S. Application Data

(60) Provisional application No. 61/660,879, filed on Jun. 18, 2012.

(51) Int. Cl.
*G01N 25/56* (2006.01)
*G01N 19/10* (2006.01)
*G01N 33/00* (2006.01)
*G01N 17/00* (2006.01)

(52) U.S. Cl.
CPC ............... *G01N 19/10* (2013.01); *G01N 33/00* (2013.01); *G01N 17/00* (2013.01)

(58) Field of Classification Search
CPC ..... G01N 31/222; G01N 21/81; G01N 19/10; G01N 31/22; G01N 2035/0424; G01N 17/00; Y10S 428/913
USPC ............. 73/73, 29.04, 29.01, 335.14, 335.07, 73/335.12, 335.13; 116/206, 216, 200, 116/209, 210, 218, 281, 283, 220, 219
See application file for complete search history.

(56) References Cited

U.S. PATENT DOCUMENTS

| 2,204,047 | A | * | 6/1940 | Otto ................................ 236/51 |
| 2,466,658 | A | * | 4/1949 | Hiltz ........................... 73/335.14 |
| 3,332,620 | A | * | 7/1967 | Streed ......................... 236/44 R |
| 3,723,393 | A | * | 3/1973 | Kistner ........................... 528/61 |
| 6,977,351 | B1 | * | 12/2005 | Woytowitz ................. 200/61.04 |
| 7,284,412 | B1 | * | 10/2007 | Perrault et al. .................... 73/40 |
| 2007/0251318 | A1 | * | 11/2007 | Holyoake .................. 73/335.05 |

* cited by examiner

*Primary Examiner* — Hezron E Williams
*Assistant Examiner* — Marrit Eyassu
(74) *Attorney, Agent, or Firm* — Fantastic IP Consulting; Eduardo E. Drake

(57) ABSTRACT

To address this and/or other needs, the present inventor devised, among other things, a passive moisture detection probe that can be installed and left in place to continuously indicate whether the moisture-content in the wall-cavity of a building is below or above a desirable level. One exemplary moisture detection assembly includes a moisture-absorbent sensor element and an indicator. The sensor element, which can be placed in contact with the inner surface of a home's exterior sheathing, expands and contracts in response to the moisture content of the sheathing. The indicator, for example a rod, moves in responsive to the expansion and contraction of the sensor element, with its relative position corresponding to the moisture in the exterior sheathing and thus providing an on-going and observable sign of moisture intrusion.

19 Claims, 7 Drawing Sheets

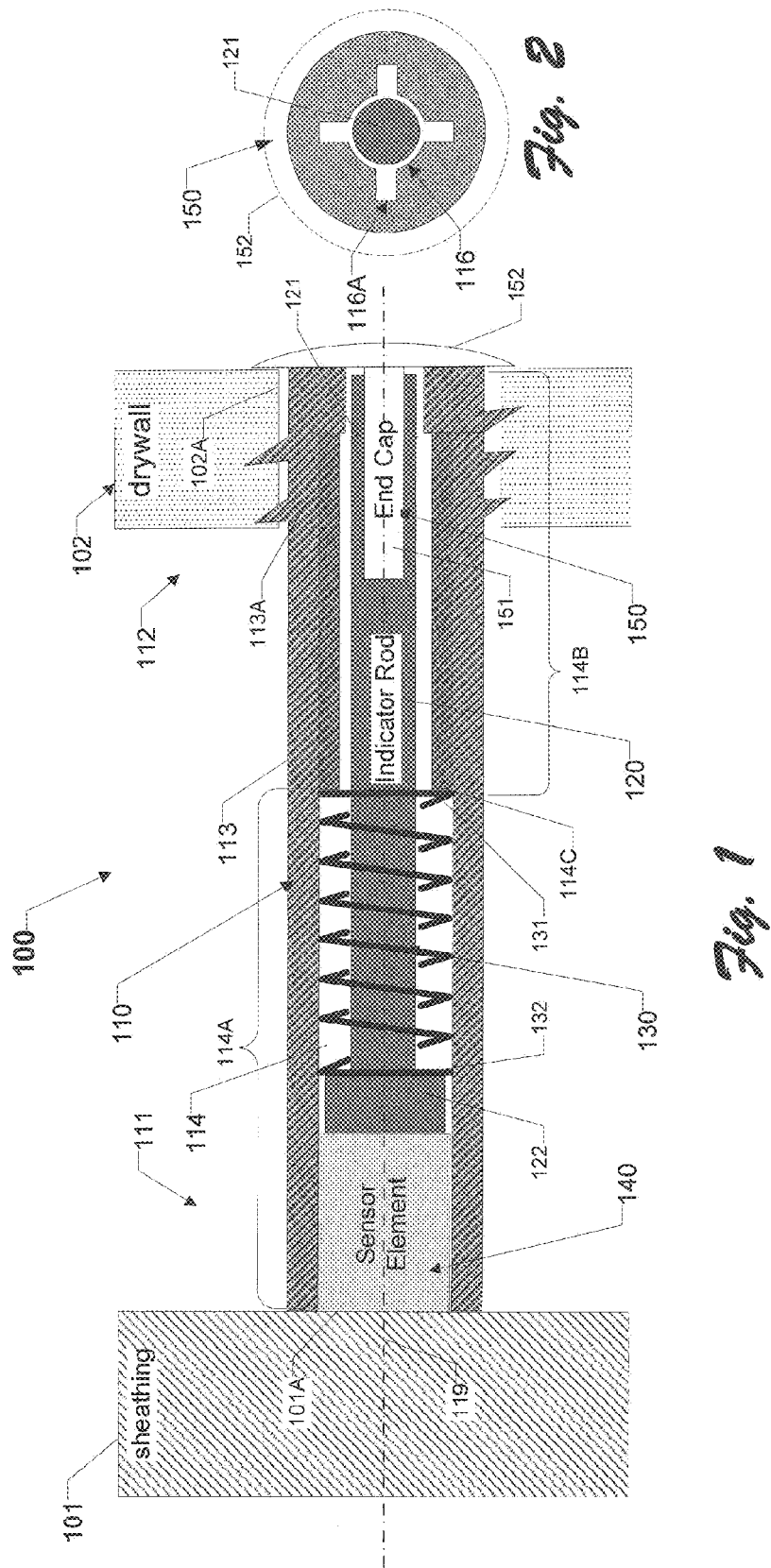

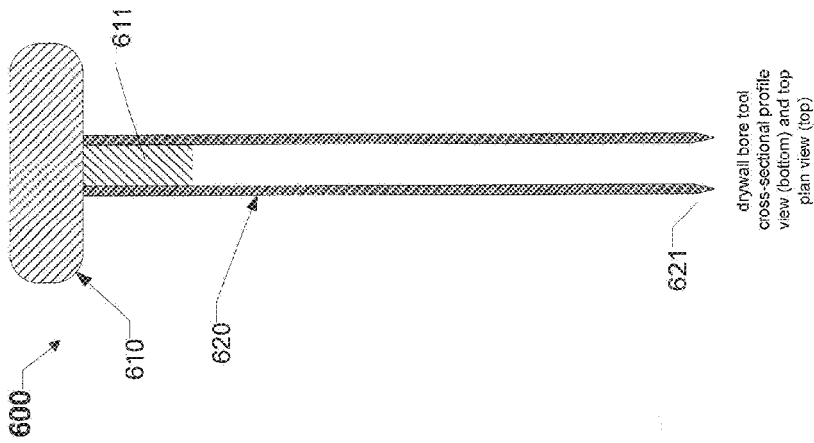
Fig. 6
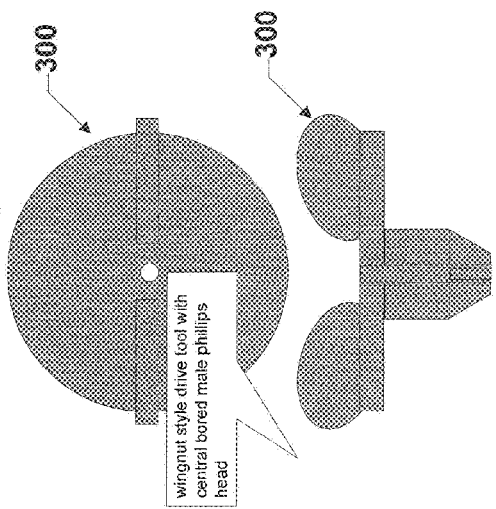
Fig. 3
Fig. 4
Fig. 5

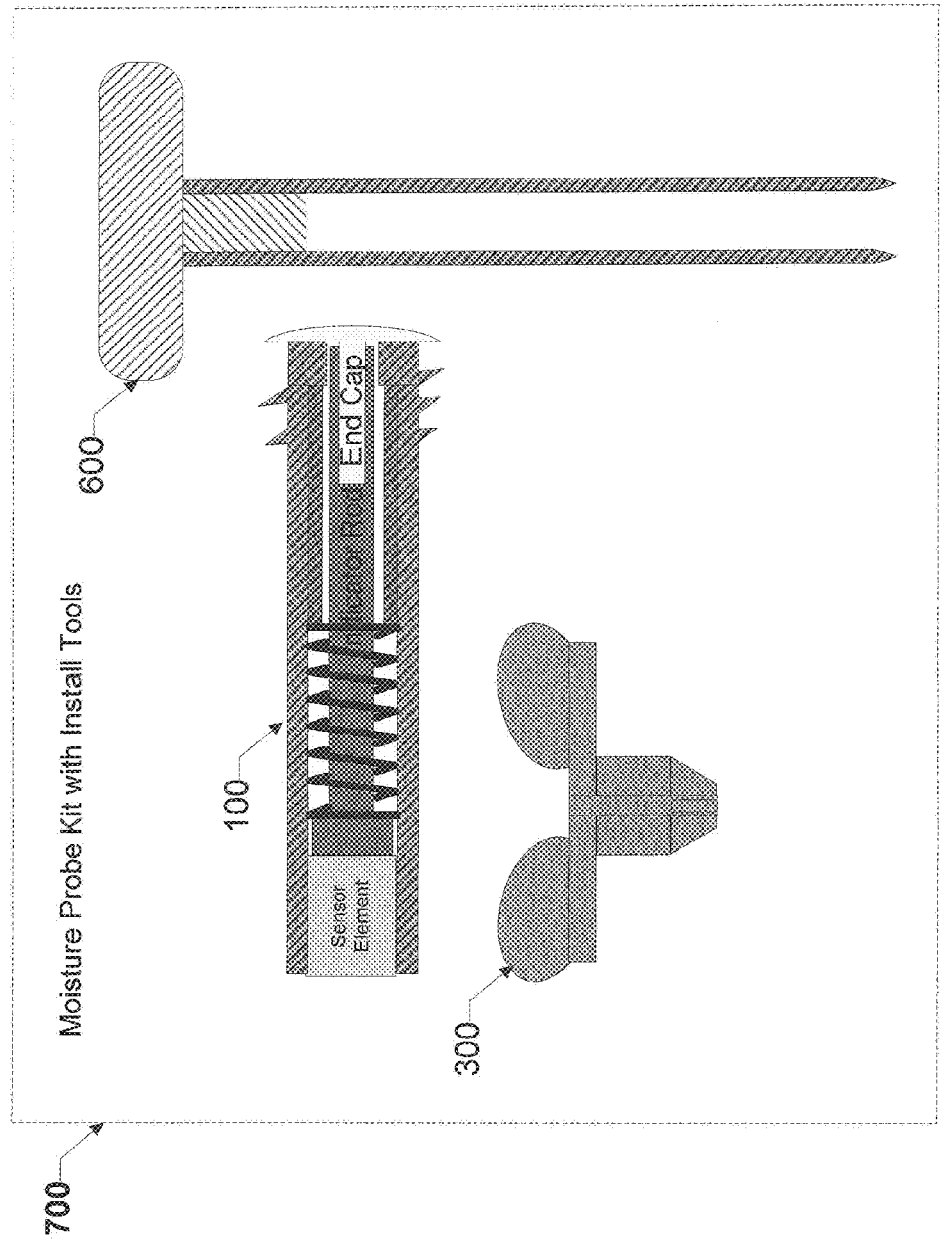

SYSTEM, COMPONENTS, AND METHODS FOR DETECTING MOISTURE

RELATED APPLICATIONS

The present application claims priority to U.S. Provisional Patent Application 61/660,879, which is incorporated herein by reference in its entirety. The present application is also the parent of co-pending application Ser. No. 14/101,150, which was filed on Dec. 19, 2013.

COPYRIGHT NOTICE AND PERMISSION

A portion of this patent document contains material subject to copyright protection. The copyright owner has no objection to the facsimile reproduction by anyone of the patent document or the patent disclosure, as it appears in the Patent and Trademark Office patent files or records, but otherwise reserves all copyrights whatsoever. The following notice applies to this document: Copyright © 2012, Alan B. Powell

TECHNICAL FIELD

Various embodiments of the present invention concern moisture detection and indication devices, particularly those suitable for use in buildings.

BACKGROUND

We have a love-hate relationship with water. We love it when it's where we need it to be, doing what we need it to do. And we hate it when it's not. The truth of this is readily known around the world by homeowners who have endured the expense, hassle, and sometimes life-threatening consequences of water intrusion into their homes, not only in the highly visible and unescapable form of seasonal flooding, but also in the elusive, often invisible form of moisture intrusion. Which can remain invisible for years until the serious damage of lost structural integrity or mold growth manifest.

For most stick-frame homes, the type most common in the United States and Canada, moisture intrusions typically occur in their wall cavities, the six-inch-thick insulation-filled space between a home's exterior siding and its interior sheetrock. The wood structure and insulation in this wall cavity can act like a large sponge, with outward signs of moisture buildup only becoming visible when the cavity is saturated and the problem is serious.

Moisture testing of all types of homes, especially stucco homes, is the best way to minimize the risk of water damage and to identify problems before they become serious. Typical testing methods require experts to measure the moisture content in the well cavities of a home. Generally, this entails drilling holes in the home's exterior siding or interior sheetrock, and inserting highly sensitive electronic moisture meters into its well cavities. Readings from the moisture meters are then recorded and the holes refilled with caulk or spackle.

The present inventor has identified at least two problems with this form of testing. The first is that the testing is generally performed only when signs of damage are already being noticed or when a home is on the market, meaning not only that most detected intrusions could have been detected and treated much earlier, but also that homeowners could have saved thousands of dollars in repair expenses. The second problem is that regular testing requires repeated drillings, probings, and refillings. This level of professional effort using expensive measuring instruments puts testing at a price point that many homeowners view as too expensive to perform regularly.

Accordingly, the present inventor has identified a need for better ways of testing for moisture in buildings.

SUMMARY

To address this and/or other needs, the present inventor devised, among other things, a passive moisture detection probe that can be installed and left in place to continuously indicate whether the moisture-content in the wall-cavity of a building is below or above a desirable level. One exemplary moisture detection assembly includes a moisture-absorbent sensor element and an indicator. The sensor element, which can be placed in contact with the inner surface of a home's exterior sheathing, expands and contracts in response to the moisture content of the sheathing. The indicator, for example a rod, moves in responsive to the expansion and contraction of the sensor element, with its relative position corresponding to the moisture in the exterior sheathing and thus providing an on-going and observable sign of moisture intrusion.

BRIEF DESCRIPTION OF DRAWINGS

FIG. 1 is a center cross-sectional view of an exemplary moisture detection assembly, which corresponds to one or more embodiments of the present invention.

FIG. 2 is an end view of the assembly in FIG. 1, corresponding to one or more embodiments of the present invention.

FIG. 3 is a top plan view of an exemplary wingnut-style driver tool for use in installing and/or removing the FIG. 1 assembly, corresponding to one or more embodiments of the present invention.

FIG. 4 is a profile view of the exemplary wingnut-style driver tool in FIG. 3, corresponding to one or more embodiments of the invention.

FIG. 5 is a profile view of the wingnut-style driver tool in FIGS. 3 and 5, corresponding to one or more embodiments of the invention.

FIG. 6 is a center cross-sectional view of an exemplary drywall bore tool for use in creating the FIG. 1 assembly, corresponding to one or more embodiments of the invention.

FIG. 7 is a schematic diagram of an exemplary kit corresponding to one or more embodiments of the present invention.

DETAILED DESCRIPTION OF EXEMPLARY EMBODIMENTS

Figure 8:
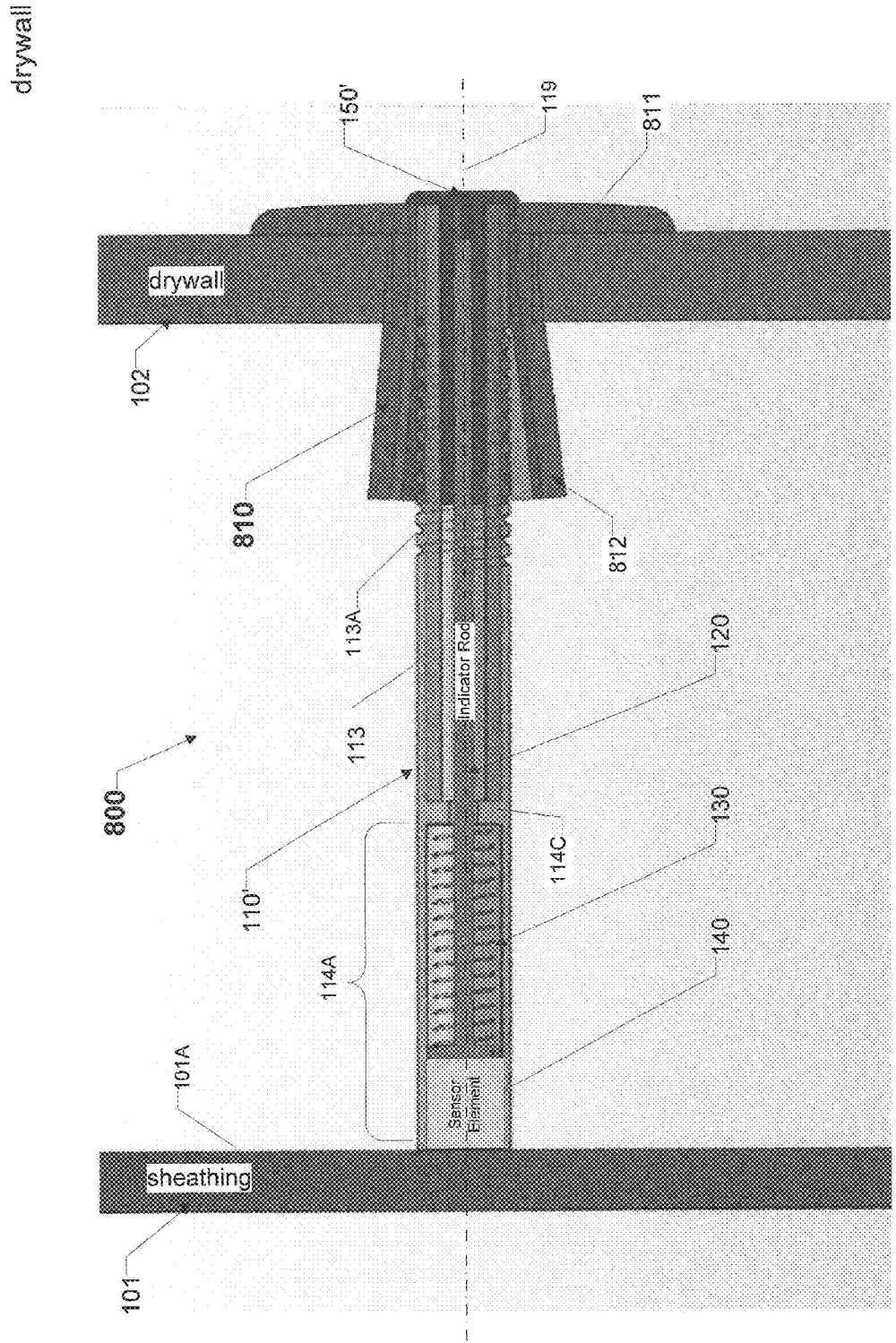
FIG. 8 is a center cross-sectional view of another exemplary moisture detection assembly, which corresponds to one or more embodiments of the present invention.

This document, which incorporates the drawings and the appended claims, describes one or more specific embodiments of one or more inventions. These embodiments, offered not to limit but only to exemplify and teach the invention, are shown and described in sufficient detail to enable those skilled in the art to implement or practice the invention(s). Thus, where appropriate to avoid obscuring the invention(s), the description may omit certain information known to those of skill in the art.

FIG. 1 shows cross-sectional view of a passive mechanical moisture detection assembly. The assembly includes an exterior wood sheathing 101 and an interior drywall or sheetrock 102, with sheathing 101 having an interior sheathing surface 101A and drywall having a bore hole 102A. (Although not shown for sake of clarity, the space between the sheathing and drywall is understood to include some form of insulation, such as a fiberglass insulation.) Inserted through bore hole 102A is an exemplary moisture detection probe assembly 100.

Probe assembly 100 includes a probe body 110, an indicator rod 120, a spring bias element 130, a moisture sensor element 140, and an end cap 150.

Probe body 110, which takes the exemplary form of a right circular cylindrical tube formed of machined, 3-D printed, injection-molded or cast-molded PVC or other durable plastic, includes a sheathing end portion 111, a drywall end portion 112, an exterior surface 113, an interior axial passage or bore 114. (Drywall and sheathing side modifiers are used as directional cues to facilitate reference to specific portions of other parts and components in this description, without necessarily using reference numbers for those specific portions. For example, indicator rod 120 has a drywall end portion, i.e. end closest to the drywall, and a sheathing end closest to the sheathing.) At the drywall end portion 112, exterior surface 113 includes integrally formed screw threads 113A which engage with drywall 102, specifically the interior surface of bore hole 102A. Axial bore 114, which extends the entire length of the probe body from the drywall end portion to the sheathing end portion, includes a first diameter region 114A and second diameter region 114C that has a smaller diameter than region 114A to define an annular ledge or step 114C. The smaller diameter of region 114C can be defined as integral dimensional change within bore 114 or by insertion of a separate right cylindrical tube within the probe body. Positioned within axial bore 114 is indicator rod 120.

Indicator rod 120, which is also form of a machined, 3-D printed, or injection-molded or cast-molded PVC or other durable plastic, includes an elongated body portion 121 and a plunger head portion 122. Elongated body portion 121 and plunger head portion 122 both take the exemplary form of a right circular cylinder, with body portion 121 being substantially longer and having a smaller diameter than plunger head portion 122. Plunger head portion 122 is larger in diameter than second diameter region 114C, so that annular ledge 114C limits axial travel or movement the indicator rod in a direction toward drywall end portion 112. Plunger head portion 122 has a sheathing side and an opposing drywall side that is integral with the elongated body portion 121 extending through spring bias element 130.

Spring bias element 130, which in the exemplary embodiment takes the form of a helical spring, has respective first and second ends 131 and 132. First end 131 is seated against annular ledge 114C, and second end 132 is seated against a drywall side of plunger head portion 122, thereby biasing the adjacent sensor element 140 into contact with interior sheathing surface 101A.

Sensor element 140, which for example takes the form a right cylindrical plug, includes a water-absorbent (more generally liquid-absorbing) material composition, which not only absorbs water but expands in size at least laterally or axially (along the lengthwise dimension of the indicator rod) during absorption. In the exemplary embodiment, the sensor element consists essentially of Hydrospan 100 material, a commercially available material composition from Industrial Polymers, Inc., 3250 South Sam Houston Parkway East, Houston, Tex. 77047. The Hydrospan 100 material generally expands uniformly in all three of its physical dimensions as it absorbs water, potentially expanding 60% by volume. The Hydrospan 100 material belongs to the Polyurethane chemical family, and has a formula maintained as a trade secret of Industrial Polymers, Inc. However, it is understood to be a reaction product of a Polyether with toluene diisocyanate (TDI).) Other embodiment may use or types of materials that also expand and/or contract, or more generally move, with changing moisture conditions. Some embodiment use composites that include the Hydrospan 100 material in combination with other absorbent or non-absorbent materials to control or restrict its expansion in certain dimensions for example dimensions perpendicular to the axial dimension of the probe body. Other potential materials include urethane resins used in diapers, and polymers used to hold and release water in soils for plant growing.

As sensor element 140 expands it pushes against plunger head portion 122 of indicator rod 120, countering the bias of spring bias element 130. With continued expansion due to persistent presence of moisture in sheathing 101, the sensor element will expand enough in size along its axial dimension to overcome the spring bias and move the rear portion (drywall end portion) of indicator rod 120 out the rear of the probe body and end cap 150 away from drywall 102, thereby providing a visual indication that a moisture condition has been detected.

End cap 150, in the exemplary embodiment, takes a plastic flange-head form and includes a neck or stem portion 151 bored to engage in an interference fit with the drywall end portion of indicator rod 120 and a flat head portion 152 integrally formed with stem portion 151. In place of end cap 150, some embodiments connect the indicator rod to actuate a normally open or normally closed electrical switch. The switch can be electrically coupled in series with an RFID (radio frequency identification) coil to disable or enable an RFID circuit or to circuitry to trigger an audible or visual alarm or to activate a wireless transmitter. In the case of the RFID coil, the switch simply couples or decouples one node or terminal of the coil from the RFID chip. Thus, an attempt to read the RFID tag, for example, will indicate either presence or nonpresence of the tag at the time of the reading.

FIG. 2 shows an end view of probe body 110, with endcap 150 removed for clarity. In this view, an opening 116 through which the elongated portion 121 of indicator rod 120 can pass is more clearly visible. Opening 116 include four prongs, of which prong 116A is representative. The prong opening allows use of a driver tool, such as the exemplary wingnut-style driver tool 300, shown in FIGS. 3, 4, and 5, to install the probe assembly such that its end is generally flush with the interior most surface of drywall 102.

FIG. 6, a center cross-sectional view, shows an exemplary drywall bore tool 600 for use in manually boring holes through drywall or sheetrock, with the holes being suitable for installation of a moisture detection probe, such as probe assembly 100, as well as for other purposes. Bore tool 600 includes a handle portion 610 and a cutting tube 620. Handle portion 610 includes a stem portion 611 which is fixedly mounted, for example threadably engaged, adhered, or welded, to cutting tube 620. Cutting tube 620, which is made of a durable metal, such as copper, bronze, steel, or aluminum, or a suitable hard and durable polycarbonate or other plastic, includes a sharpened cutting end 621. The end may be formed to include sawtooth teeth in some embodiments.

In use, one positions the cutting end of the tube on the location of a desired hole in sheetrock or drywall and uses the handle to push the tool into the drywall, while turning or reciprocating the handle back and forth, in clockwise and counterclockwise directions, until the cutting tube penetrates the drywall. The tool can then be worked with less effort to cut through insulation, thereby forming an effective bore hole or tunnel for installing probe assembly 100, or other suitable purposes. In the exemplary embodiment, cutting tube 620 forms holes approximately 0.5 or 0.625 inches in diameter to cooperate with a slightly smaller probe body diameter.

FIG. 7 shows an exemplary moisture detection kit 700. In the exemplary embodiment, kit 700 includes one or more moisture probe assemblies, such as probe assembly 100 (or 800 in FIG. 8), one or more bore tools, such as bore tool 600 or bore tool (1200 in FIG. 11), and one or more installation driver tools, such as wingnut-style driver tool 300.

FIG. 8 shows an exemplary moisture probe assembly 800, which is similar in structure and function to assembly 100 in FIG. 1. The main difference between assembly 800 and assembly 100 is the inclusion of a guide tube 810.

Figure 9:
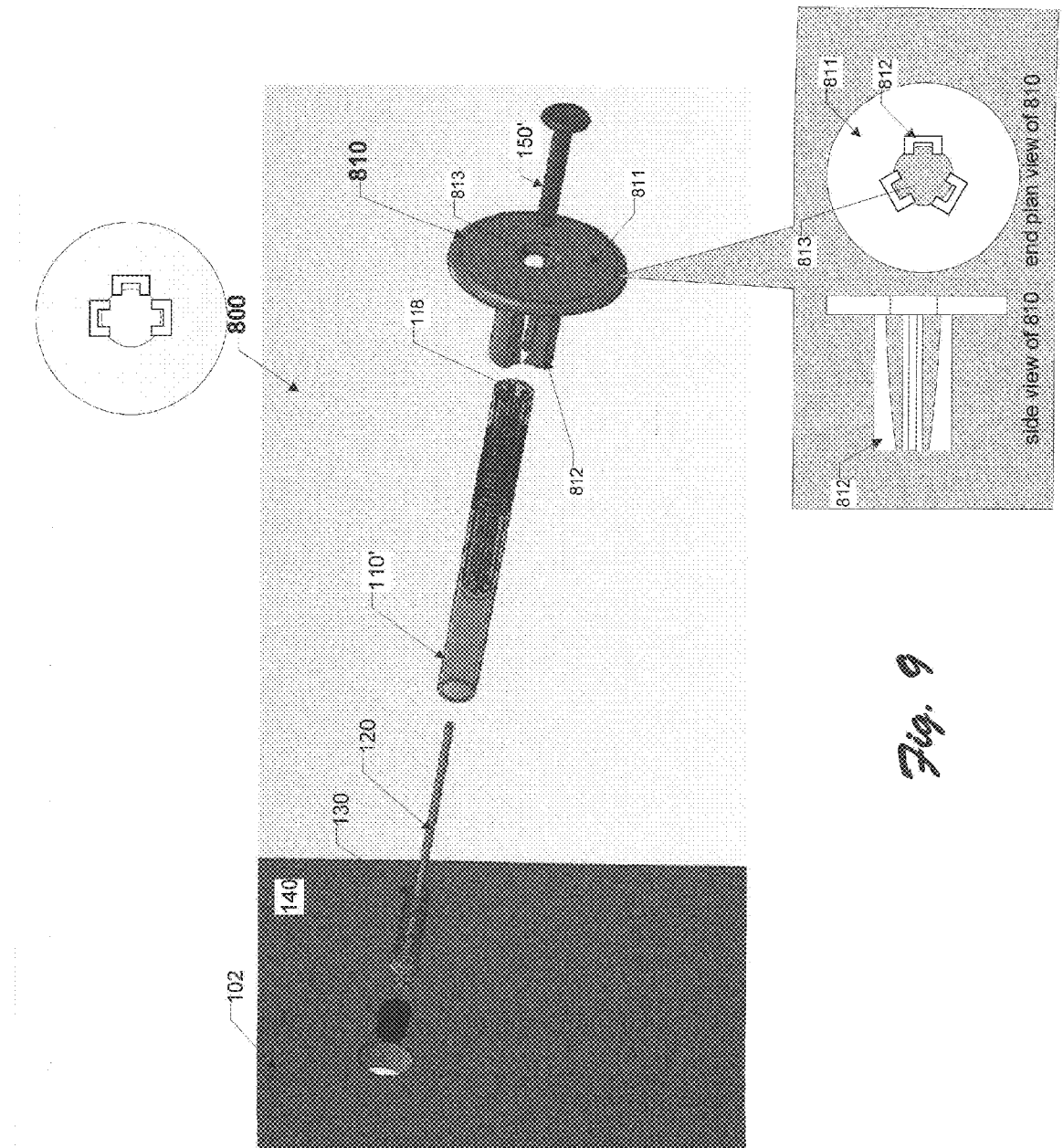
FIG. 9 is an exploded isometric view of the FIG. 8 moisture detection assembly and thus corresponds to one or more embodiments of the present invention.

More specifically, guide tube 810 not only anchors probe body 110' to drywall 102, but also ensures that it is substantially perpendicularly to the surface of drywall 102 and sheathing 101, thereby ensuring that the sheathing side of sensor element 140 fully contacts surface 101A. It is believed that deviation from full endface contact of the sensor element with the monitored surface (surface 101A) will result in less than optimal performance of the moisture detection probe assembly, since moisture will likely force the sensor element to expand beyond containment of the probe body and thereby reduce transfer of axial expansion force to indicator rod 120. Guide tube 810 (probe guide tube), shown best in FIG. 9, includes a face 811, and two or more, for example 3 or 4, leaf-spring prongs 812, and opening 813. Leaf-spring prongs 812, are formed as tapered U-channels with the taper increasing with distance away from face plate. Thus, when inserted into a drywall hole and probe body 110' is passed through opening 813, the probe body spreads the leaf-spring prongs into frictional engagement with the interior surface of the drywall hole, anchoring the guide tube in place. The probe body may then be pushed flush to sheathing surface ends of the Other differences between assembly 800 and 100 include an endcap 150' which receives the elongated body portion of indicator rod 120, internal longitudinal ribs 820 (best seen in FIG. 9) within the axial passage of probe body 110', substitution of flattened exterior threads 113A' on probe body 110.

Figure 10:
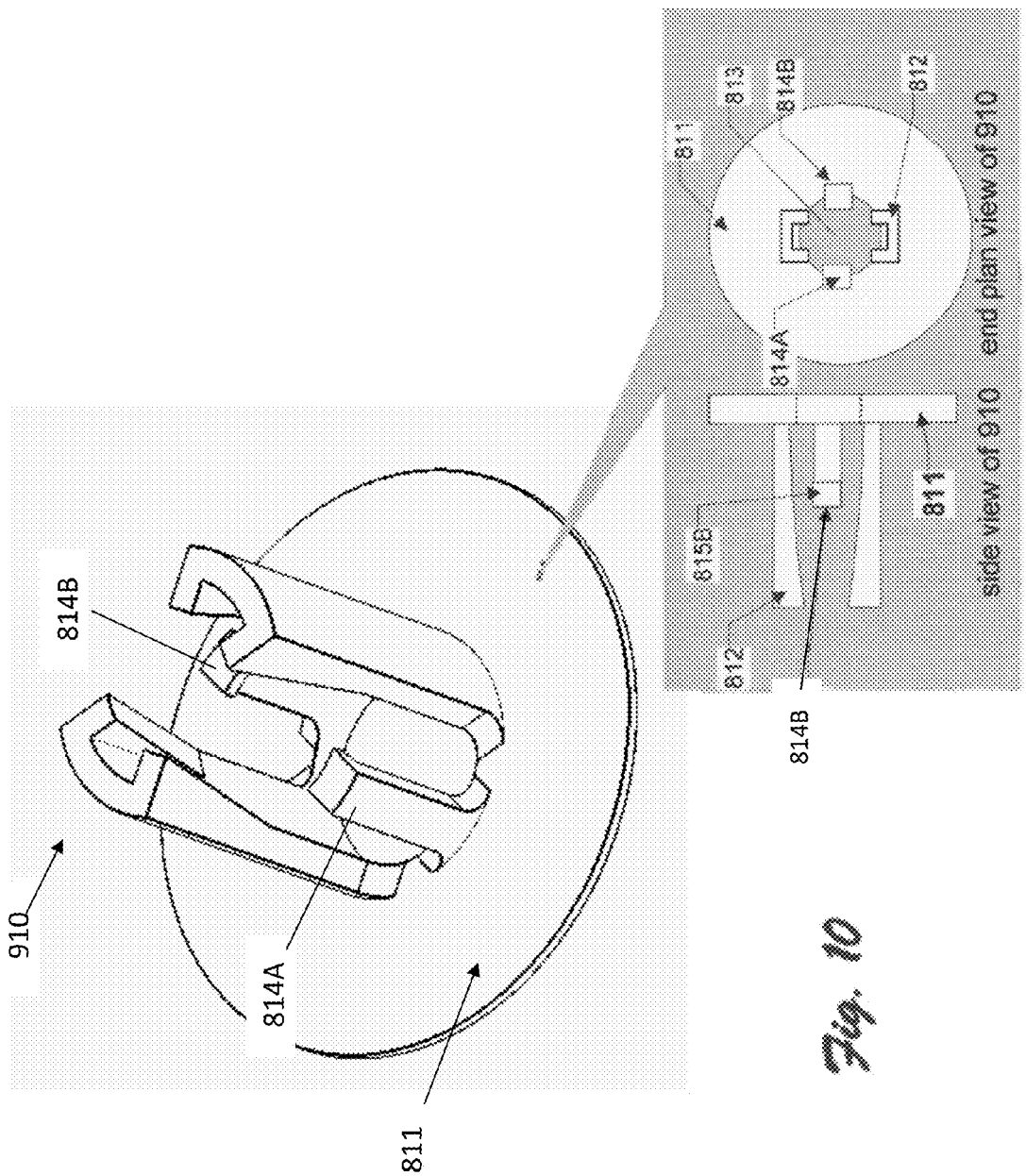
FIG. 10 is an alternative form of a guide tube portion of the FIG. 8 moisture detection assembly, which corresponds to one or more embodiments of the present invention.

FIG. 10 shows an side and perspective views of an alternative guide tube 910 which may be used in place of guide tube 810. In contrast to guide tube 810 which includes three leaf-spring prongs of substantially equally length, probe guide tube 910 includes two leaf-spring prongs 812 and two opposing thread prongs 814A and 814B, which are about half as long as the leaf-spring prongs and which include respective cleats or protrusions 815A and 815B to better engage with threads 113A on probe body 110' and thus better ensure the desired perpendicular alignment with sheathing surface 101A.

Figure 11:
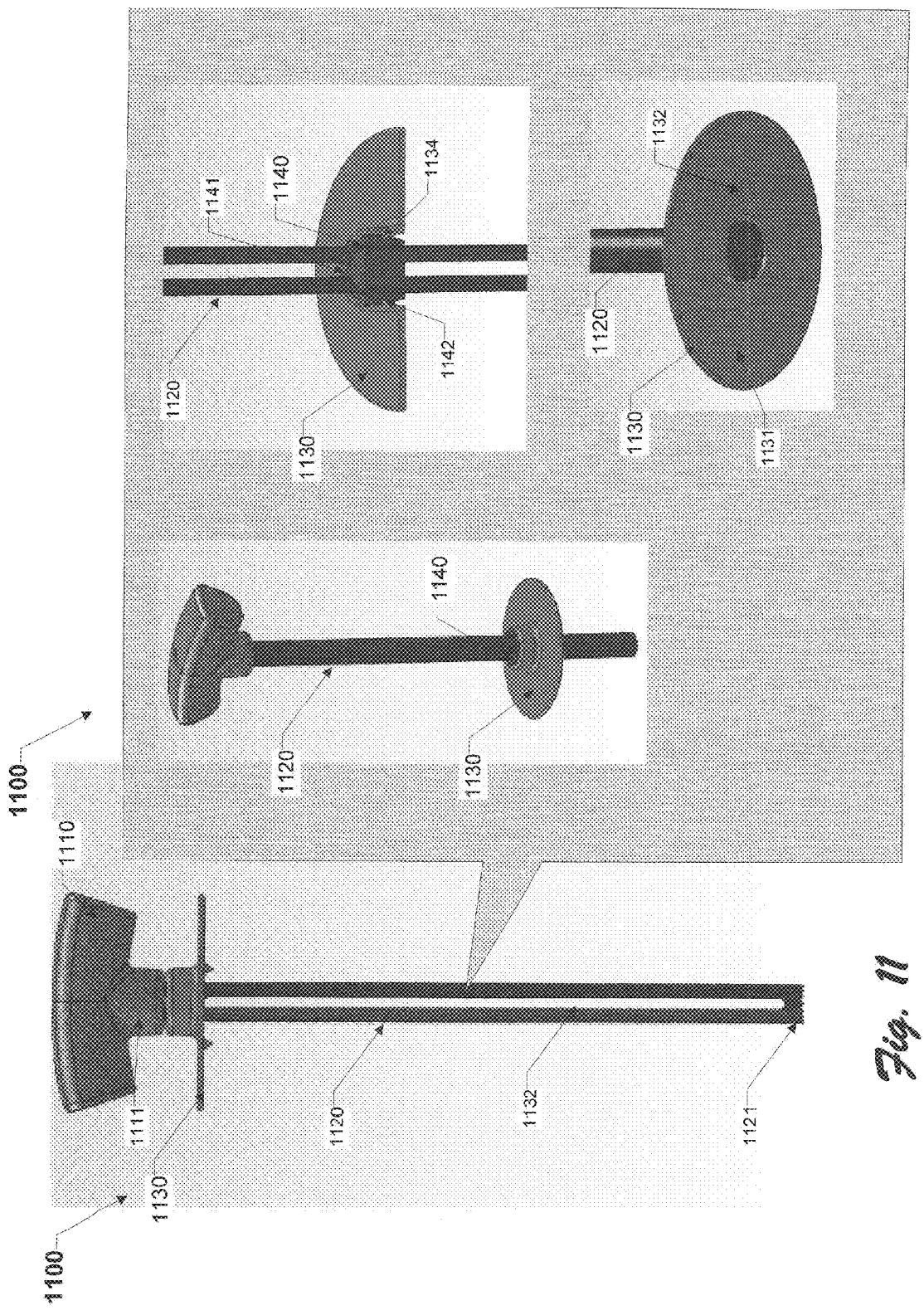
FIG. 11 is a front perspective view of an alternative drywall bore tool, which may be used in place of the FIG. 6 bore tool, and which corresponds to one or more embodiments of the invention.

FIG. 11 shows a profile view of an alternative exemplary drywall bore tool 1100, which is similar in basic function and structure of drywall bore tool 600 in FIG. 6, with the exception of some added features to ensure higher precision boring and efficiency. Bore tool 1100 includes a handle portion 1110 and a slotted cutting tube 1120, a bore guide plate 1130, and a bore guide ring 1140. Handle portion 1110 includes a stem portion 1111 which is fixedly mounted, for example threadably engaged, adhered, or welded, to slotted cutting tube 1120. Cutting tube 1120, which is made of a durable metal, such as copper, bronze, steel, or aluminum, or a suitable hard and durable polycarbonate or other plastic, includes a sharpened cutting end 1121 and a longitudinal slot 1123. The longitudinal slot runs to the top end of the tube to allow full assembly of the tool, though this is not visible in the figure because of handle stem portion 1111. Bore guide plate 1130 includes a bottom face 1131 with protrusions 1132 to engage the surface of the drywall being bored and to ensure stable position of the tool during boring operations. Plate 1130 also includes a guide stem portion 1133 with an annular guide ridge 1134. Bore guide ring 1140 includes a slot engagement member 1141 that engages with slot 1123, enabling the bore guide ring to slide freely along the length of the cutting tube between the cutting end and the handle. Bore guide ring 1140 also includes an annular groove 1142 that slideably engages via snap fit with annular guide ridge 1134, defining a lateral rotational plane for the guide ring that is substantially parallel to bottom face 1131. In operation, a user manually places the guide plate over the desired bore location and pushes the cutting tube into the drywall surface (generally substrate surface) using the handle. The handle is then worked back and forth, as with tool 600, with the guide plate and guide ring ensuring perpendicular boring through the drywall and beyond.

CONCLUSION

The embodiments described above are intended only to illustrate and teach one or more ways of practicing or implementing the present invention, not to restrict its breadth or scope. Nothing presented herein is intended to be construed as critical, required, or essential to the invention as claimed. The actual scope of the invention, which embraces all ways of practicing or implementing the teachings of the invention, is defined only by the following claims including any amendments made during pending of the application and all equivalents of those claims as issued.

Moreover in this document, relational terms, such as second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter

What is claimed is:

1. A method of detecting a moisture condition in a building wall having wall cavity defined by an exterior sheathing portion and an interior drywall portion opposite the exterior sheathing portion, the method comprising:
   placing a water-absorbent material in contact with an interior surface of the exterior sheathing portion so that the material can absorb water that may infiltrate the exterior sheathing portion; and
   indicating detection of the moisture condition in response to the water-absorbent material expanding and pushing a portion of an indicator outside the wall cavity from a first position to a second position.

2. The method of claim 1, wherein the water-absorbent material includes a Hydroxy Terminated Poly (Oxyalkylene) Polyol.

3. The method of claim 1, further comprising actuating an electrical switch in response to movement of the indicator to the second position; and wherein movement of the indicator to the second position indicates a moisture condition of at least 20%.

4. The method of claim 1, wherein moving at least a portion of an indicator outside the wall cavity from a first portion to second position, includes compressing a spring configured to bias the indicator toward the interior surface.

5. A passive moisture detection assembly comprising:
   an elongated structure configured to extend across a wall cavity defined by an interior surface of a sheathing wall of a building and an interior wall of the building;
   a material composition configured for expansion or contraction in response to ambient moisture, the material composition positioned at a first end of the elongated structure to contact the interior surface of the sheathing wall and to absorb water that may infiltrate the sheathing wall; and
   an indicator having a portion positioned at a second end of the elongated structure and configured to be pushed outside the wall cavity and away from the first end of the elongated structure by the material composition in response to moisture-induced expansion of the material composition.

6. The assembly of claim 5:
   wherein the material composition defines at least a portion of a sensor element;
   wherein the elongated structure has a length dimension and includes an axial passage generally parallel to the length dimension; and
   wherein the indicator comprises a rod portion and a cap portion, with the rod portion extending through the axial passage and having a first end contacting the sensor element and a second end connected to the cap portion, with the cap portion having a portion configured for placement outside the wall cavity.

7. The assembly of claim 5, wherein the material composition consists essentially of a Hydroxy Terminated Poly (Oxyalkylene) Polyol.

8. The assembly of claim 5, wherein the material composition comprises a reaction product of a polyether with toluene diisocyanate.

9. The assembly of claim 5:
   wherein the material composition defines at least a portion of a sensor element;
   wherein the elongated structure defines a chamber having first and second end portions and an intermediate portion extending between the first and second end portions, with the first end portion at least partially containing the sensor element and the indicator including a rod extending through the intermediate portion and at least partially into the second end portion.

10. The assembly of claim 9:
    wherein the rod has an end rod portion at least partially within the second end portion of the chamber; and
    wherein the assembly further includes an end cap having a head portion at least partially outside the wall cavity and a stem portion extending from the head portion into the second end portion of the chamber to connect with the end rod portion.

11. The assembly of claim 10:
    wherein the second end portion of the chamber extends at least partially through the interior wall; and
    wherein the assembly further includes means, coupled to the second end of the chamber, for keeping the chamber substantially perpendicular to the interior surface of the sheathing wall.

12. The assembly of claim 11, wherein the means for keeping the chamber substantially perpendicular to the interior surface of the sheathing wall includes a plate having an opening and two or more prongs extending perpendicularly from the plate through a hole in the interior wall into the wall cavity.

13. A moisture detection assembly for at least partial placement within a wall cavity of a building, the wall cavity defined by an exterior sheathing wall and an interior wall, the assembly comprising:
    housing means for extending across the wall cavity and holding a water-absorbent material in contact with an interior surface of the exterior sheathing wall; and
    means, at least partially within the housing means and responsive to expansion of the water-absorbent material, for pushing an indicator outside the wall cavity to indicate a moisture condition within the sheathing wail.

14. The moisture detection assembly of claim 13, wherein the water-absorbent material consists essentially of a reaction product of a polyether with toluene diisocyanate.

15. The moisture detection assembly of claim 13:
    wherein the water-absorbent material at least partially defines a sensor element;
    wherein the means for moving at least a portion of an indicator includes a rod having a first end coupled to the sensor element and a second end coupled to an end cap that is at least partially outside the wall cavity and adjacent to the interior wall; and wherein the means for extending across the wall cavity includes a tubular housing enclosing a least a portion of the rod and a portion of the sensor element.

16. The moisture detection assembly of claim 15, further comprising a spring element within the housing for biasing the sensor element into contact with the sheathing wall.

17. The moisture detection assembly of claim 13, wherein the assembly further comprises means, coupled to the means for extending across the wall cavity, for keeping the means for extending substantially perpendicular to the interior surface.

18. The moisture detection assembly of claim 17, wherein the means for keeping the housing means substantially perpendicular includes a plate having an opening and two or more prongs extending perpendicularly from the plate through a hole in the interior wall into the wall cavity.

19. The moisture detection assembly of claim 18, wherein second end portion of the chamber extends through the opening in the plate to engage with and cause the two or more prongs to spread open against sides of the hole in the interior wall.

* * * * *